(12) United States Patent
Bhadra et al.

(10) Patent No.: US 10,828,485 B2
(45) Date of Patent: Nov. 10, 2020

(54) HIGH-CHARGE CAPACITY ELECTRODES TO DELIVER DIRECT CURRENT NERVE CONDUCTION BLOCK

(71) Applicant: Case Western Reserve University, Cleveland, OH (US)

(72) Inventors: Narendra Bhadra, Chesterland, OH (US); Jesse Wainright, Willoughby Hills, OH (US); Niloy Bhadra, Cleveland Heights, OH (US); Kevin L. Kilgore, Avon Lake, OH (US); Tina Vrabec, Willoughby Hills, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 140 days.

(21) Appl. No.: 15/760,246

(22) PCT Filed: Sep. 30, 2016

(86) PCT No.: PCT/US2016/054663
§ 371 (c)(1),
(2) Date: Mar. 15, 2018

(87) PCT Pub. No.: WO2017/062272
PCT Pub. Date: Apr. 13, 2017

(65) Prior Publication Data
US 2018/0256886 A1 Sep. 13, 2018

Related U.S. Application Data

(60) Provisional application No. 62/237,660, filed on Oct. 6, 2015.

(51) Int. Cl.
*A61N 1/04* (2006.01)
*A61N 1/20* (2006.01)
*A61N 1/36* (2006.01)

(52) U.S. Cl.
CPC ......... *A61N 1/0436* (2013.01); *A61N 1/0408* (2013.01); *A61N 1/0472* (2013.01); *A61N 1/20* (2013.01); *A61N 1/36062* (2017.08)

(58) Field of Classification Search
CPC .. A61N 1/0472; A61N 1/0436; A61N 1/3606; A61N 1/0408; A61N 1/20
See application file for complete search history.

(56) References Cited

U.S. PATENT DOCUMENTS 3,911,899 A 10/1975 Hattes
4,057,069 A 11/1977 Dorffer et al.
(Continued)

FOREIGN PATENT DOCUMENTS

DE 4324185 1/1995
EP 3606599 2/2020
(Continued)

OTHER PUBLICATIONS

Abidian, Mohammad Reza, and David C. Martin. "Multifunctional nanobiomaterials for neural interfaces." Advanced Functional Materials 19.4 (2009): 573-585.
(Continued)

*Primary Examiner* — Catherine M Voorhees
(74) *Attorney, Agent, or Firm* — Tarolli, Sundheim, Covell & Tummino LLP (57) ABSTRACT

The present disclose generally relates to high-charge capacity electrodes that include a substrate and a coating covering at least a portion of the substrate that includes active particles held together by a biocompatible binding material. One aspect of the present disclosure relates a system that can block conduction in a nerve. The system can include a current generator that generates a direct current (DC). The system can also include a high-charge capacity electrode
(Continued)

that can be coupled to the current generator to deliver the DC to block conduction in a nerve.

6 Claims, 6 Drawing Sheets

(56) References Cited

U.S. PATENT DOCUMENTS

| | | | |
|---|---|---|---|
| 5,401,970 | A | 3/1995 | Kinsey et al. |
| 6,293,266 | B1 | 9/2001 | Oetting |
| 7,620,453 | B1 | 11/2009 | Propato et al. |
| 2002/0120309 | A1 | 8/2002 | Richmond et al. |
| 2004/0127953 | A1 | 7/2004 | Kilgore et al. |
| 2005/0197675 | A1 | 9/2005 | David et al. |
| 2006/0100668 | A1 | 5/2006 | Ben-David |
| 2007/0043400 | A1 | 2/2007 | Donders et al. |
| 2007/0060815 | A1 | 3/2007 | Martin et al. |
| 2007/0067004 | A1 | 3/2007 | Boveja et al. |
| 2007/0073354 | A1 | 3/2007 | Knudson et al. |
| 2007/0083193 | A1 | 4/2007 | Werneth et al. |
| 2007/0255319 | A1 | 11/2007 | Greenberg et al. |
| 2007/0291522 | A1 | 12/2007 | Toba et al. |
| 2008/0208287 | A1 | 8/2008 | Palermo et al. |
| 2008/0208300 | A1 | 8/2008 | Pasch |
| 2008/0243196 | A1 | 10/2008 | Libbus et al. |
| 2009/0036945 | A1 | 2/2009 | Chancellor et al. |
| 2009/0192567 | A1 | 7/2009 | Armstrong et al. |
| 2009/0254148 | A1 | 10/2009 | Borgens et al. |
| 2010/0016929 | A1 | 1/2010 | Prochazka |
| 2010/0241190 | A1 | 9/2010 | Kilgore et al. |
| 2010/0274314 | A1 | 10/2010 | Alataris et al. |
| 2010/0280500 | A1 | 11/2010 | Skelton et al. |
| 2011/0021943 | A1 | 1/2011 | Lacour et al. |
| 2011/0071513 | A1 | 3/2011 | Shin et al. |
| 2011/0077660 | A1 | 3/2011 | Janik et al. |
| 2011/0125216 | A1 | 5/2011 | Kilgore et al. |
| 2011/0160798 | A1* | 6/2011 | Ackermann, Jr. ... A61N 1/0551 607/46 |
| 2011/0190849 | A1 | 8/2011 | Faltys et al. |
| 2011/0192720 | A1 | 8/2011 | Blauw et al. |
| 2011/0221438 | A1 | 9/2011 | Goodwill et al. |
| 2012/0016226 | A1 | 1/2012 | Gertner |
| 2012/0053510 | A1 | 3/2012 | Peters et al. |
| 2012/0277829 | A1 | 11/2012 | Chow et al. |
| 2013/0006331 | A1 | 1/2013 | Weisgarber et al. |
| 2013/0035745 | A1 | 2/2013 | Ahmed et al. |
| 2013/0053922 | A1 | 2/2013 | Ahmed et al. |
| 2013/0079838 | A1 | 3/2013 | Libbus et al. |
| 2013/0238048 | A1 | 9/2013 | Almendinger et al. |
| 2013/0274842 | A1 | 10/2013 | Gaunt et al. |
| 2014/0031905 | A1 | 1/2014 | Irazoqui et al. |
| 2014/0119480 | A1 | 5/2014 | Keegan |
| 2014/0257438 | A1* | 9/2014 | Simon ............... A61N 1/0456 607/72 |
| 2014/0324129 | A1 | 10/2014 | Franke et al. |
| 2015/0073406 | A1 | 3/2015 | Molsberger |
| 2015/0148878 | A1* | 5/2015 | Yoo ............... A61N 1/0472 607/118 |
| 2015/0165210 | A1 | 6/2015 | Kilgore et al. |
| 2015/0174397 | A1 | 6/2015 | Bhadra et al. |
| 2015/0182742 | A1 | 7/2015 | Ackermann et al. |
| 2015/0238764 | A1 | 8/2015 | Franke |
| 2015/0272657 | A1 | 10/2015 | Yates et al. |
| 2016/0101286 | A1* | 4/2016 | Bhadra ............... A61N 1/3615 607/46 |
| 2016/0158542 | A1 | 6/2016 | Ahmed |
| 2016/0235969 | A1 | 8/2016 | Kilgore et al. |
| 2016/0235990 | A1 | 8/2016 | Mashiach |
| 2016/0243353 | A1 | 8/2016 | Ahmed |
| 2016/0256689 | A1 | 9/2016 | Vallejo et al. |
| 2016/0263381 | A1 | 9/2016 | Ahmed et al. |
| 2016/0271392 | A1 | 9/2016 | Vallejo et al. |
| 2016/0271413 | A1 | 9/2016 | Vallejo et al. |
| 2016/0331326 | A1 | 11/2016 | Xiang et al. |
| 2016/0346533 | A1 | 12/2016 | Bhadra et al. |
| 2017/0028192 | A1 | 2/2017 | Ahmed et al. |
| 2017/0050024 | A1 | 2/2017 | Bhadra et al. |
| 2017/0080244 | A1 | 3/2017 | Chiel et al. |
| 2017/0100591 | A1 | 4/2017 | Nudo et al. |
| 2017/0136235 | A1 | 5/2017 | Molsberger |
| 2017/0312505 | A1 | 11/2017 | Ahmed |
| 2018/0028824 | A1 | 2/2018 | Pivonka et al. |
| 2018/0256886 | A1 | 9/2018 | Bhadra et al. |
| 2018/0361155 | A1 | 12/2018 | Bhadra et al. |
| 2019/0060640 | A1 | 2/2019 | Bhadra et al. |
| 2019/0167996 | A1 | 6/2019 | Bhadra et al. |
| 2019/0184160 | A1 | 6/2019 | Franke et al. |
| 2019/0184173 | A1 | 6/2019 | Franke |
| 2019/0269921 | A1 | 9/2019 | Bhadra et al. |
| 2019/0314630 | A1 | 10/2019 | Ackermann et al. |
| 2020/0001073 | A1 | 1/2020 | Bhadra et al. |

FOREIGN PATENT DOCUMENTS

| | | |
|---|---|---|
| JP | 2010540104 A | 12/2010 |
| JP | 2015519184 A | 7/2015 |
| WO | 2007/082382 | 7/2007 |
| WO | 2008/140376 | 11/2008 |
| WO | 2010/042750 | 4/2010 |
| WO | 2013/188753 A1 | 12/2013 |
| WO | 2014/167063 A1 | 10/2014 |
| WO | 2015/142838 | 9/2015 |
| WO | 2017/044542 | 3/2017 |
| WO | 2017/062272 | 4/2017 |
| WO | 2017/106519 | 6/2017 |
| WO | 2018/085611 | 5/2018 |
| WO | 2018/187237 | 10/2018 |
| WO | 2019/157285 | 8/2019 |
| WO | 2019/164952 | 8/2019 |
| WO | 2020/010020 | 1/2020 |

OTHER PUBLICATIONS

Australian Examination Report for corresponding Australian Application Serial No. 2016335931, dated Sep. 14, 2018, pp. 1-9.
Accornero, Neri, et al. "Selective Activation of peripheral nerve fibre groups of different diameter by triangular shaped stimulus pulses." The Journal of Physiology 273.3 (1977): 539-560.
Ackermann, D. Michael, et al. "Effect of nerve cuff electrode geometry on onset response firing in high-frequency nerve conduction block." IEEE Transactions on Neural Systems and Rehabilitation Engineering 18.6 (2010): 658-665.
Ackermann, D. Michael, et al. "Conduction block of whole nerve without onset firing using combined high frequency and direct current." Medical & biological engineering & computing 49.2 (2011): 241-251.
Bhadra, Niloy, and Kevin L. Kilgore. "Direct current electrical conduction block of peripheral nerve." IEEE Transactions on Neural Systems and Rehabilitation Engineering 12.3 (2004): 313-324.
Bhadra, Niloy, and Kevin L. Kilgore. "High-frequency electrical conduction block of mammalian peripheral motor nerve." Muscle & Nerve: Official Journal of the American Association of Electrodiagnostic Medicine 32.6 (2005): 782-790.
Bhadra, Narendra, et al. "Selective suppression of sphincter activation during sacral anterior nerve root stimulation." Neurourology and Urodynamics: Official Journal of the International Continence Society 21.1 (2002): 55-64.
Brummer, S. B., and M. J. Turner. "Electrical stimulation with Pt electrodes: II-estimation of maximum surface redox (theoretical non-gassing) limits." IEEE Transactions on Biomedical Engineering 5 (1977): 440-443.
Cangiano, A., and Lodovico Lutzemberger. "The action of selectively activated group II muscle afferent fibers on extensor motoneurons." Brain research 41.2 (1972): 475-478.
Casey, Kenneth L., and Marjorie Blick. "Observations on anodal polarization of cutaneous nerve." (1969).
Coleridge, Hazel M., et al. "Impulses in slowly conducting vagal fibers from afferent endings in the veins, atria, and arteries of dogs and cats." Circulation Research 33.1 (1973): 87-97.

(56) References Cited

OTHER PUBLICATIONS

Feltham, A. M., and Michael Spiro. "Platinized platinum electrodes." Chemical Reviews 71.2 (1971): 177-193.

Franke, Manfred, et al. "Combined KHFAC+ DC nerve block without onset or reduced nerve conductivity after block." Journal of neural engineering 11.5 (2014): 056012.

Guz, A., and Diana W. Trenchard. "The role of non-myelinated vagal afferent fibres from the lungs in the genesis of tachypnoea in the rabbit." The Journal of physiology 213.2 (1971): 345-371.

Hopp, Francis A., and Jeanne L. Seagard. "Respiratory responses to selective blockade of carotid sinus baroreceptors in the dog." American Journal of Physiology-Regulatory, Integrative and Comparative Physiology 275.1 (1998): R10-R18.

Hopp, Francis A., et al. "Effect of anodal blockade of myelinated fibers on vagal C-fiber afferents." American Journal of Physiology-Regulatory, Integrative and Comparative Physiology 239.5 (1980): R454-R462.

Kato, M., and K. Fukushima. "Effect of differential blocking of motor axons on antidromic activation of Renshaw cells in the cat." Experimental brain research 20.2 (1974): 135-143.

Kilgore, Kevin L., and Niloy Bhadra. "Reversible nerve conduction block using kilohertz frequency alternating current." Neuromodulation: Technology at the Neural Interface 17.3 (2014): 242-255.

Kilgore, Kevin L., and N. Bhadra. "Nerve conduction block utilising high-frequency alternating current." Medical and Biological Engineering and Computing 42.3 (2004): 394-406.

Manfredi, M. "Differential block of conduction of larger fibers in peripheral nerve by direct current." Archives italiennes de biologie 108.1 (2018): 52-71.

McCloskey, D. I., and J. H. Mitchell. "The use of differential nerve blocking techniques to show that the cardiovascular and respiratory reflexes originating in exercising muscle are not mediated by large myelinated afferents." The Journal of physiology 222.1 (1972): 50P.

McCreery, D. B., et al. "Comparison of neural damage induced by electrical stimulation with faradaic and capacitor electrodes." Annals of biomedical engineering 16.5 (1988): 463-481.

Merrill, Daniel R., Marom Bikson, and John GR Jefferys. "Electrical stimulation of excitable tissue: design of efficacious and safe protocols." Journal of neuroscience methods 141.2 (2005): 171-198.

Mills, Allan. "Final Analysis: Porous Platinum Morphologies: Platinised, Sponge and Black." (2007).

Petruska, Jeffrey C., Charles H. Hubscher, and Richard D. Johnson. "Anodally focused polarization of peripheral nerve allows discrimination of myelinated and unmyelinated fiber input to brainstem nuclei." Experimental brain research 121.4 (1998): 379-390.

Ravid, Einat, and Arthur Prochazka. "Controlled nerve ablation with direct current: parameters and mechanisms." IEEE Transactions on Neural Systems and Rehabilitation Engineering 22.6 (2014): 1172-1185.

Rijkhoff, N. J. M., et al. "Selective detrusor activation by electrical sacral nerve root stimulation in spinal cord injury." The Journal of urology 157.4 (1997): 1504-1508.

Sant'Ambrogio, G., M. Decandia, and L. Provini. "Diaphragmatic contribution to respiration in the rabbit." Journal of applied physiology 21.3 (1966): 843-847.

Sassen, Michael, and Manfred Zimmermann. "Differential blocking of myelinated nerve fibres by transient depolarization." Pflügers Archiv 341.3 (1973): 179-195.

Sawyer, Donald T., Andrzej Sobkowiak, and Julian L. Roberts. Electrochemistry for chemists. Wiley, 1995.

Schuettler, Martin. "Electrochemical properties of platinum electrodes in vitro: comparison of six different surface qualities." Engineering in Medicine and Biology Society, 2007. EMBS 2007. 29th Annual International Conference of the IEEE. IEEE, 2007.

Shannon, Robert V. "A model of safe levels for electrical stimulation." IEEE Transactions on Biomedical Engineering 39.4 (1992): 424-426.

Thoren, Peter, John T. Shepherd, and David E. Donald. "Anodal block of medullated cardiopulmonary vagal afferents in cats." Journal of Applied Physiology 42.3 (1977): 461-465.

Vrabec, Tina, et al. "Use of high surface area electrodes for safe delivery of direct current for nerve conduction block." ECS Transactions 50.28 (2013): 31-37.

Whitwam, J. G., and C. Kidd. "The use of direct current to cause selective block of large fibres in peripheral nerves." British journal of anaesthesia 47.11 (1975): 1123-1132.

Zecevic, S. K., et al. "Kinetics of O 2 reduction on a Pt electrode covered with a thin film of solid polymer electrolyte." Journal of the Electrochemical Society 144.9 (1997): 2973-2982.

Zimmermann, Manfred. "Selective activation of C-fibers." Pflüger's Archiv für die gesamte Physiologie des Menschen und der Tiere 301.4 (1968): 329-333.

Australia Examination report No. 1 for standard patent application for corresponding Australia Application Serial No. 2016335931, dated Jun. 6, 2018, pp. 1-3.

PCT International Search Report and Written Opinion for International Application Serial No. PCT/US2016/054663, dated Jan. 5, 2017, pp. 1-11.

Ackermann, Jr, D. Michael, et al. "Separated interface nerve electrode prevents direct current induced nerve damage." Journal of neuroscience methods 201.1 (2011): 173-176.

Borsook, David. "A future without chronic pain: neuroscience and clinical research." Cerebrum: the Dana forum on brain science. vol. 2012. Dana Foundation, 2012.

Brummer, S.B. et al. "Electrical Stimulation of the Nervous System: The Principle of Safe Charge Injection with Noble Metal Electrodes." Bioelectrochemistry and Bioenergetics 2: (1975) 13-25.

Bussel, Catelijne M., Dirk L. Stronks, and Frank JPM Huygen. "Successful treatment of intractable complex regional pain syndrome type I of the knee with dorsal root ganglion stimulation: a case report." Neuromodulation: Technology at the Neural Interface 18.1 (2015): 58-61.

Cogan, S.F., et al. "In Vitro Comparison of the Charge-Injection Limits of Activated Iridium Oxide (AIROF) and Platinum-Iridium Microelectrodes", IEEE Transactions on Biomedical Engineering, 52.9 (2005): 1612-1614.

Cogan, S.F., et al. "Potential-Biased, Asymmetric Waveforms for Charge-Injection With Activated Iridium Oxide (AIROF) Neural Stimulation Electrodes." 2006: 53(2): 327-332.

Donaldson et al. "When are actively balanced biphasic ('Lilly') stimulating pulses necessary in a neurological prosthesis?" Medical & Biological Engineering & Computing Jan. 1986: 24: 41-49.

Elbasiouny, S., et al. Modulation of motoneuronal firing behavior after spinal cord injury using intraspinal microstimulation current pulses: a modeling study. J. Appl. Physiol. 103 (2007) 276-286.

Fridman, Gene Y., and Charles C. Della Santina. "Safe direct current stimulation to expand capabilities of neural prostheses." IEEE Transactions on Neural Systems and Rehabilitation Engineering 21.2 (2013): 319-328.

Fridman, Gene Y., and Charles C. Della Santina. "Safe direct current stimulator 2: concept and design." In Engineering in Medicine and Biology Society (EMBC), 2013 35th Annual International Conference of the IEEE, pp. 3126-3129. IEEE, 2013.

Gabrielsson, Erik O., et al. "A four diode full wave ionic current rectifier based on bipolar membranes: Overcoming the limit of electrode capacity." Advanced Materials 26.30 (2014): 5143-5147.

Hasegawa, G., et al. "Impact of Electrolyte on Pseudocapacitance and Stability of Porous Titanium Nitride (TiN) Monolithic Electrode", Journal of the Electrochemical Society, 162.1 (2015): A77-A85.

Hollingworth, Milo, et al. "Single Electrode Deep Brain Stimulation with Dual Targeting at Dual Frequency for the Treatment of Chronic Pain: A Case Series and Review of the Literature." Brain sciences 7.1 (2017): 1-11.

Holtzheimer, Paul E., and Helen S. Mayberg. "Deep brain stimulation for psychiatric disorders." Annual review of neuroscience 34 (2011): 289-307.

Huang, C. et al. "Electrical stimulation of the auditory nerve: direct current measurement in vivo." IEEE Transactions on Biomed. Eng. vol. 46 No. 4 Apr. 1999 at 461-470.

Hurlbert, R. John. "Dose-response study of the pathologic effects of chronically applied direct current stimulation on the normal rat spinal cord." J. Neurosurg. 79 (Dec. 1993) 905-916.

(56) References Cited

OTHER PUBLICATIONS

Keifer, Orion Paul, Jonathan P. Riley, and Nicholas M. Boulis. "Deep brain stimulation for chronic pain: intracranial targets, clinical outcomes, and trial design considerations." Neurosurgery Clinics 25.4 (2014): 671-692.

Kim et al. "Electrochemical studies on the alternating current corrosion of mild steel under cathodic protection condition in marine environments", Electrochimica Acta 51, 2006, p. 5259-5267.

Krum, Henry, et al. "Catheter-based renal sympathetic denervation for resistant hypertension: a multicentre safety and proof-of-principle cohort study." The Lancet 373.9671 (2009): 1275-1281.

Kumsa, D et al. Electrical neurostimulation with imbalanced waveform mitigates dissolution of platinum Electrodes. J. Neural Eng. 13 (2016): 1-5.

Kumsa, D et al. Electrical neurostimulation with imbalanced waveform mitigates dissolution of platinum electrodes. Neural Eng. (2018) 13(5): 1-8.

Kumsa, D.W., et al. "Electron transfer processes occurring on platinum neural stimulating electrodes: pulsing experiments for cathodic-first, charge-imbalanced, biphasic pulses for 0.566 ? k ? 2.3 in rat subcutaneous tissues", Journal of Neural Engineering, 16 (2019): 1-11.

McHardy, J., et al., "An Approach to Corrosion Control during Electrical Stimulation", Annals of Biomedical Engineering, 5 (1977): 144-149.

Mendell, Lorne M. "Constructing and deconstructing the gate theory of pain." Pain® 155.2 (2014): 210-216.

Mortimer, J.T., et al., "Intramuscular Electrical Stimulation: Tissue Damage", Annals of Biomedical Engineering, 8 (1980): 235-244.

Nahin, Richard L. "Estimates of pain prevalence and severity in adults: United States, 2012." The Journal of Pain 16.8 (2015): 769-780.

Nakajima, H., et al. "Cervical angina: a seemingly still neglected symptom of cervical spine disorder?" Spinal cord 44.8 (2006): 509-513.

Neupane, M et al. Study of Anodic Oxide Films of Titanium Fabricated by Voltammetric Technique in Phosphate Buffer Media. Int. J. Electrochem. Sci., 4 (2009) 197-207.

Nielsen et al., "AC-Corrosion and Electrical Equivalent Diagrams", in: Proceedings of 5th International Congress, CeoCo, bruxelles, Belgium, 2000.

Schaldach M, Fractal Coated Leads: Advanced Surface Technology of Genuiune Sensing and Pacing, Progress in Biomedical Research, (2000): 259-272.

Scheiner, A., et al., "Imbalanced Biphasic Electrical Stimulation: Muscle Tissue Damage", Annals of Biomedical Engineering, 18 (1990): 407-425.

Specht, H. et al., Electrochemical properties and stability of PVD coatings for the application in cardiac and neurological stimulation, (2006).

TJEPKEMACloostermans, Marleen C., et al. "Effect of burst stimulation evaluated in patients familiar with spinal cord stimulation." Neuromodulation: Technology at the Neural Interface 19.5 (2016): 492-497.

Yang, Fei, et al. "Differential expression of voltage-gated sodium channels in afferent neurons renders selective neural block by ionic direct current." Science advances 4.4 (2018): eaaq1438 in 10 pages.

Japanese Office Action for corresponding Japanese Application Serial No. 2018-515952, dated Jun. 29, 2020, pp. 1-3.

* cited by examiner

HIGH-CHARGE CAPACITY ELECTRODES TO DELIVER DIRECT CURRENT NERVE CONDUCTION BLOCK

RELATED APPLICATION

This application claims priority to U.S. Provisional Application Ser. No. 62/237,660, filed Oct. 6, 2015, entitled "SYSTEMS AND METHODS FOR DIRECT CURRENT NERVE CONDUCTION BLOCK", the entirety of which is hereby incorporated by reference for all purposes.

TECHNICAL FIELD

The present disclosure relates generally to a high-charge capacity electrode to deliver direct current (DC) nerve conduction block and, more specifically, to systems and methods to deliver the DC nerve conduction block safely using the high-charge capacity electrode.

BACKGROUND

Many neurological diseases are characterized by unwanted neural activity conducted along peripheral axons and inducing pathological effects at the end organs. Although kilohertz frequency alternating current (KHFAC) nerve conduction block has been widely explored and appeared promising, it has not been adopted clinically due to the production of an undesirable onset response in the nerve. While it is possible to completely neutralize the onset response by applying a brief DC waveform through a flanking electrode, nerve conduction is lost after several applications of the DC waveform.

DC nerve conduction block has become an attractive candidate for achieving block without the onset response. Indeed, application of a DC alone can produce a complete conduction block without the onset response of the KHFAC nerve conduction block. Additionally, anodic break excitation at cessation can be prevented by the design of the DC nerve conduction block waveform. However, the likelihood of the DC nerve conduction block causing damage to the nerve (e.g., due the production of non-reversible Faradaic reaction products during stimulation) has kept the DC nerve conduction block from being adopted clinically.

SUMMARY

The present disclosure relates generally to a high-charge capacity electrode to deliver direct current (DC) nerve conduction block to a nerve without causing damage to the nerve. Such high-charge capacity electrodes can apply the DC nerve conduction block, while avoiding the generation of the damaging non-reversible Faradaic reaction products. Accordingly, the present disclose relates to systems and methods to deliver the DC nerve conduction block safely using the high-charge capacity electrode.

In one aspect, the present disclosure can include a high-charge capacity electrode that can be used to deliver DC to a nerve to block conduction in the nerve when coupled to a current generator. The high-charge capacity electrode can include a substrate and a coating covering at least a portion of the substrate. The coating can include high surface area nano-particles held together by a biocompatible binder material.

In another aspect, the present disclosure can include a system that can block conduction in a nerve. The system can include a current generator that generates a DC. The current generator can be coupled to a high-charge capacity electrode that can deliver the DC to block conduction in the nerve. The high-charge capacity electrode can include a substrate and a coating covering at least a portion of the substrate that includes active particles held together by a biocompatible binding material.

In a further aspect, the present disclosure can include a method for altering conduction in a nerve. A high-charge capacity electrode, coupled to a current generator, can be placed in proximity to a nerve. The high-charge capacity electrode can include a substrate and a coating covering at least a portion of the substrate. The coating can include active particles held together by a biocompatible binder material. A DC, generated by the current generator, can be applied to the nerve. The DC can have an amplitude sufficient to alter transmission of action potentials in the nerve. The transmission of the action potentials in the nerve can be altered based on the applied DC without causing damage to the nerve and/or the high-charge electrode as a result of electrochemical reaction products.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "direct current nerve conduction block" or "DC nerve conduction block" can refer to the application of a direct current to a nerve to alter conduction in the nerve.

As used herein, the terms "direct current" or "DC" can refer to a current pulse of either polarity (e.g., either cathodic or anodic). In some instances, the DC can be applied as the first phase of a biphasic waveform. The second phase of the biphasic waveform can either reverse 100% of the total charge delivered by the first phase (as a charge-balanced biphasic waveform) or reverse less than 100% of the total charge delivered by the first phase (as a charge imbalanced biphasic waveform), thereby reducing the production of damaging reaction products that can cause damage to the nerve and/or the electrodes used to deliver the DC.

As used herein, the term "pseudocapacitor" can refer to an electrochemical capacitor that stores electrical charge in a Faradaic fashion by electron charge transfer between electrode and electrolyte. This is accomplished through electrosorption, redox reactions, and intercalation processes.

As used herein, the term "damaging reaction products" can refer to the irreversible reaction products of Faradaic reactions generated as a result of DC application. These irreversible reaction products can be from an unwanted side reaction that generates the damaging reaction products. An example can be found in the oxidation of water to oxygen, in which some electrons are diverted to the production of hydrogen peroxide, which can be irreversible.

As used herein, the terms "alter" or "altering", when used with reference to nerve conduction, can refer to affecting or changing a manner in which action potentials are conducted in a nerve. In some instances, nerve conduction can be altered by extinguishing an action potential at some point as it travels along the nerve (also referred to as "blocking" nerve conduction). In other instances, nerve conduction can be altered by increasing the activation threshold of a nerve and/or decreasing the conduction velocity of a nerve (also referred to as "attenuating" nerve conduction).

As used herein, the term "nerve conduction block" can refer to blocking and/or attenuating nerve conduction. Nerve conduction is "blocked" when transmission of action potentials through a target nerve is extinguished completely (e.g., 100% extinguished) as the action potentials travel through the nerve. The block can be achieved by depolarization or hyperpolarization of the nerve membrane comprising the target nerve.

As used herein, the term "incomplete block" can refer to a partial block, where less than 100% (e.g., less than about 90%, less than about 80%, less than about 70%, less than about 60%, or less than about 50%) of the action potentials traveling through a target nerve are extinguished. Nerve conduction is "attenuated" when an "incomplete nerve block" occurs. In one example, when nerve conduction is attenuated, a target nerve will have an increased activation threshold and thereby make the target nerve more difficult to excite.

As used herein, a nerve conduction block can be considered "safe" when the block occurs without producing non-reversible reaction products.

As used herein, the term "nerve" can refer to one or more fibers that employ electrical and chemical signals to transmit motor, sensory, and/or autonomic information from one body part to another. A nerve can refer to either a component of the central nervous system or the peripheral nervous system.

As used herein, the term "neurological disorder" can refer to a condition or disease characterized at least in part by abnormal conduction in one or more nerves. In some instances, a subject suffering from a neurological disorder can experience pain and/or muscle spasticity. Examples of neurological disorders can include stroke, brain injury, spinal cord injury (SCI), cerebral palsy (CP), multiple sclerosis (MS), etc.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

As used herein, the term "medical professional" can refer to an individual who provides care to a patient. A medical professional can be, for example, a doctor, a physician's assistant, a student, a nurse, a caregiver, or the like.

II. Overview

The present disclosure relates generally to a high-charge capacity electrode to deliver direct current (DC) nerve conduction block and, more specifically, to systems and methods to deliver the DC nerve conduction block safely using the high-charge capacity electrode. DC nerve conduction block is attractive because it does not suffer from onset response and can be designed to avoid anodic break. However, DC nerve conduction block has not been used clinically due to its high likelihood of causing nerve damage at the charge required to be delivered for DC nerve conduction block (e.g., due to the generation of non-reversible Faradaic reaction products). Advantageously, the high-charge capacity electrode described herein is designed to avoid such nerve damage. As discussed in more detail below, the high-charge capacity electrode of the present disclosure provides several advantages over other types of electrodes in terms of mechanical stability and the amount of charge able to be delivered. For example, platinized platinum is able to deliver the charge required for nerve conduction block, but is well known to suffer from poor mechanical properties, which result in rapid and significant losses in surface area (and, therefore, charge capacity), thereby creating uncertainty as to the charge capacity during and after implantation. As another example, iridium oxide electrodes can be used, exploiting the high capacitive/low impedance properties of iridium oxide. While iridium oxide is generally stable, the charge storage capacity of iridium oxide is still 1-2 orders of magnitude below what is required for nerve conduction block. In contrast, the high-charge capacity electrodes employed by the systems and methods described herein have a high charge capacity and robust mechanical properties that enable the use of DC nerve conduction block in a variety of clinical and experimental applications.

III. Systems

One aspect of the present disclosure can include a system 10 (FIG. 1) that can deliver a DC nerve conduction block (e.g., monophasic, balance charged bipasic, or charge imbalanced biphasic) to alter (e.g., block or attenuate) conduction in a nerve. The system 10 can include components for generating a current (e.g., current generator 12), as well as components to apply the current to the nerve (e.g., high-charge capacity electrode 14). In one example, the nerve can be a peripheral nerve (e.g., motor, sensory, and/or autonomic) or a nerve or nervous tissue comprising the central nervous system (e.g., brain and/or spinal cord). The DC nerve conduction block can be used to treat various neurological disorders including, but not limited to, pain or muscle spasticity. Advantageously, the high-charge capacity electrode 14 is capable of (1) delivering the charge required for nerve conduction block applications, while avoiding the generation of damage-causing non-reversible reaction products, and (2) exhibiting robust mechanical properties so that the charge can be predictably delivered. In other words, the system 10 can deliver the DC nerve conduction block safely at least because of the high-charge capacity electrode 14 design and the waveform generated by the current generator 12.

Figure 1:
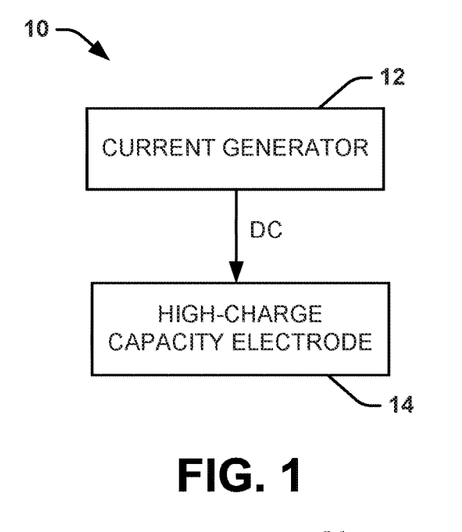
FIG. 1 is a schematic diagram showing a system that can deliver a direct current (DC) nerve conduction block in accordance with an aspect of the present disclosure.

As shown in FIG. 1, the system 10 can include a current generator 12 to generate the DC, and a high-charge capacity electrode 14 to apply the DC to a nerve. The high-charge capacity electrode 14 can be electrically coupled to the current generator 12. In some instances, the high-charge capacity electrode 14 can be in electrical communication with the current generator 12 via a wired connection. In other instances, the high-charge capacity electrode 14 can be in electrical communication with the current generator 12 via a wireless connection and/or a combination of a wired connection and a wireless connection.

The current generator 12 can be configured or programmed to generate a DC of sufficient amplitude to cause the nerve conduction block. In some instances, the DC used for nerve conduction block can require a current with a large amplitude to be delivered to the nerve. For example, the current required may be 2 mA for 10 seconds, requiring a total electrical charge to be transferred of approximately 20 mC or more. Accordingly, the current generator 12 can be any device configured or programmed to generate the specified current for application to a nerve to achieve an alternation in conduction thereof. One example of a current generator 12 is a battery-powered, portable generator. Another example of a current generator 12 is an implantable generator (IPG). It will be appreciated that the current generator 12 can include additional components to selectively configure the current waveform, such as an amplitude modulator (not shown).

In some instances, the generated DC can have an anodic polarity or a cathodic polarity, and an amplitude sufficient to cause the nerve conduction block. In some instances, the current generator 12 can be configured or programmed to generate a DC having a biphasic waveform, with one phase cathodic and one anodic. In this case, the altering DC can be delivered to the nerve in the first phase for a specific period of time, while a second phase having an opposite polarity can reduce or eliminate unwanted effects (e.g., due to irreversible reaction products) generated by the first phase. The unwanted effects can be generated and reversed at the high-charge capacity electrode 14 and/or at the electrode-electrolyte interface.

In some instances, a generated biphasic DC waveform can be a charge-balanced biphasic waveform that produces zero net charge. In other instances, a generated biphasic DC waveform can be applied as a substantially charge-balanced DC waveform that produces a small net charge to reduce reaction products that are damaging to the nerve and/or the high-charge capacity electrode 14. Advantageously, the current generator 12 can be configured or programmed to a DC having a biphasic waveform, which allows nerve conduction to be altered without damaging the nerve itself and/or producing systemic side-effects.

The high-charge capacity electrode 14 can deliver the DC to the nerve to achieve the nerve conduction block. In some instances, the high-charge capacity electrode 14 can have a capacitance per area of about 50 mF/cm$^2$ or more. In other instances, the high-charge capacity electrode 14 can have a capacitance per area of about 75 mF/cm$^2$. In still other instances, the high-charge capacity electrode 14 can have a capacitance per area of about 100 mF/cm$^2$ or more. The high-charge capacity electrode 14 can exhibit the large capacitance per area with a predictability of the area. In some instances, depending on the materials chosen for the high-charge capacity electrode 14, charge recovery can serve to extend the life of the high-charge capacity electrode 14. Since the DC nerve conduction block has a low duty cycle, there is sufficient time between large pulse deliveries of a polarity to allow for low amplitude trickle recharge of the opposite polarity. Periodic reversal of the delivery current prevents a large voltage from building on the charged high-charge capacity electrode 14.

Figure 2:
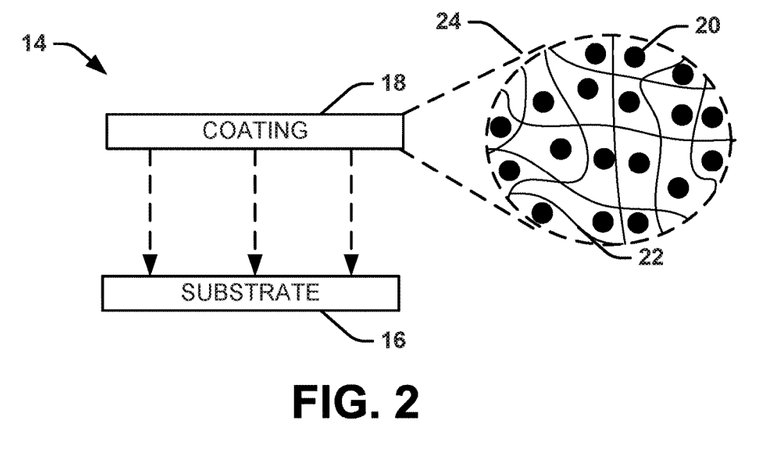
FIG. 2 is a schematic diagram of the high-charge capacity electrode in FIG. 1.

As shown in FIG. 2, the high-charge capacity electrode 14 can include a substrate 16 and a coating 18. In some instances, selection of materials to use as the substrate 16 and coating 18 can be based on a combination of charge capacity, durability, ease of manufacture, and availability. The substrate 16 can be any type of electrically-conductive material (e.g., stainless steel, gold, silver, platinum, or the like). As an example, the substrate 16 can be a platinum foil or a platinum wire. The coating 18 can cover at least a portion of the substrate 16. In some instances, the coating 18 can cover the entire substrate 16. In other instances, the coating 18 can cover at least 50% of the substrate 16. In still other instances, the coating 18 can cover a portion of the substrate 16 in contact with or exposed to the nerve.

The coating 18 can be biocompatible and stable with routine charging and discharging of the DC. In some instances, the coating 18 can provide an electronic double layer capacitor (EDLC), an electrochemical capacitor for which energy storage is achieved through the double layer capacitance of the high-charge capacity electrode 14. The coating 18 can be highly reproducible and does not produce any harmful reaction products (e.g., by introduce any foreign ions into the electrolyte or change the pH of the environment).

The coating 18 can include active particles 20 held together by a biocompatible binder material 22, as shown in magnified region 24. The active particles 20, when held together by the binder material 22, can yield the high-charge capacity electrode 14 with a high charge capacity. The specific number of active particles 20 can vary and is based, at least in part, on the necessary charge capacity, the active particle material used, and the binder material 22 used. Similarly, the binder material 22 can be arranged in any different molecular configuration, as long as it can provide mechanical stability to hold the active particles 20 together.

The active particles 20 can be made of one or more non-Faradaic materials. In some instances, the active particles 20 can include high surface area nano-particles. For example, the nano-particles can be carbon based nano-particles (e.g., biological carbon, such as YP-50 or YP-80 high surface area activated carbon). In another example, the nano-particles can be platinum nano-particles, iridium oxide nano-particles, or any number of other biocompatible nano-particles. In some instances, the nano-particles can all be of the same material. In other instances, the nano-particles can be made of a variety of different materials. In one example, the nano-particles can have a surface area of at least about 500 $m^2/g$, at least about 750 $m^2/g$, or at least about 1,000 $m^2/g$.

The binder material 22 can adhere to the substrate 16 and hold the active particles 20 in place. Accordingly, the binder material 22 can be a material that can provide good adhesion, is durable, and is biocompatible. As one example, the binder material 22 can be a biocompatible polymer material. Example biocompatible polymer materials include Nafion, polyvinyl alcohol, Teflon, polyvinylidene fluoride (PVDF), and the like. The choice of an appropriate binder material 22 can facilitate the high-charge capacity of the high-charge capacity electrode 14.

In one example, the active particles 20 can be carbon while the binder material 22 is Nafion or PVDF. The carbon active particles 20 can be made with an extremely high level of porosity, thereby resulting in very high surface areas. For example, the surface area can be 1,000-3,000 or more $m^2$ of surface area/g of carbon. When placed in an electrolyte solution, the electrochemical capacitance of the carbon active particles 20 can be on the order of 100-600 F/g. Thus, a very small amount of carbon material can store a significant amount of electrical charge. If the capacitance is normalized to the geometric area of the high-charge capacity electrode 14, the capacitance is on the order of 100-2,500 $mF/cm^2$. Since the charging and discharging mechanism involves only the motion of ions in the electrolytes and electrons within the carbon, these carbon active particles 20 can create a capacitor that can be routinely charged and discharged over 100,000 times. In this example, the high-charge capacity electrode 14 can have a capacitance of 40 mF to provide 20 mC charge required. A 30 square mm surface that is coated with carbon active particles 20 can have a specific capacitance of 350 $mF/cm^2$ and a capacitance of 100 mF, thereby allowing the high-charge capacity electrode 14 to store enough charge for DC nerve block applications.

IV. Methods

Another aspect of the present disclosure can include a method 30 (FIG. 3) for delivering DC nerve conduction block to a nerve. The method 30 can be executed using the system 10 shown in FIG. 1 and described above. Advantageously, the high-charge capacity electrode 14 of the system 10 can be capable of delivering the charge required for nerve conduction block applications, while avoiding the generation of damage-causing non-reversible reaction products and exhibiting robust mechanical properties so that the charge can be predictably delivered. In other words, the method 30 can deliver the DC nerve conduction block safely without generating irreversible reaction products, thereby increasing patient safety and increasing the potential for clinical adoption.

Figure 3:
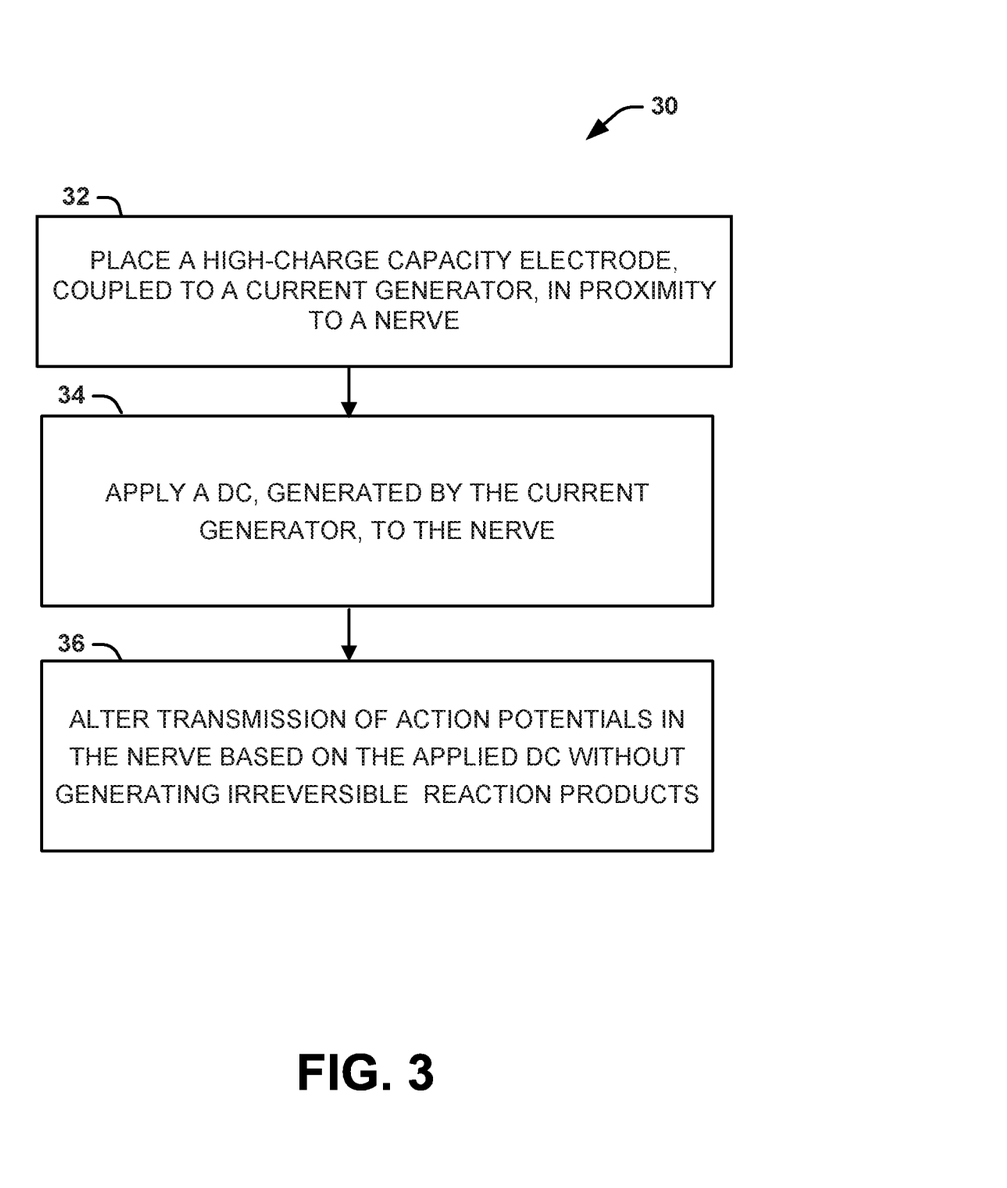
FIG. 3 is a process flow diagram illustrating a method for delivering DC nerve conduction block according to another aspect of the present disclosure.

The method 30 can generally include the steps of: placing a high-charge capacity electrode, coupled to a current generator, in proximity to a nerve (Step 32); applying a DC, generated by the current generator, to the nerve (Step 34); and altering transmission of action potentials in the nerve based on the applied DC without generating irreversible reaction products (Step 36). The method 30 is illustrated as process flow diagrams with flowchart illustrations. For purposes of simplicity, the method 30 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method 30.

At Step 32, a high-charge capacity electrode (e.g., element 14) is coupled to a current generator (e.g., element 12) and placed in proximity to a nerve. In some examples, the nerve can be a peripheral nerve (e.g., motor, sensory, and/or autonomic) or a nerve or nervous tissue comprising the central nervous system (e.g., brain and/or spinal cord). As an example, the high-charge capacity electrode can be placed alongside the nerve. The DC nerve conduction block can be used to treat various neurological disorders including, but not limited to, pain or muscle spasticity. The high-charge capacity electrode can be made of a substrate and a coating covering at least a portion of the substrate. The coating can include active particles held together by a biocompatible binder material. An effective block can occur when the high-charge capacity electrode crosses perpendicular to the long axis of the nerve.

At Step 34, the current generator can be activated to generate a DC. The generated DC can be applied to the nerve by the high-charge capacity electrode. The DC can have an amplitude sufficient to alter transmission of action potentials in the nerve. For example, the applied DC can be anodic or cathodic and have an amplitude sufficient to generate an electric field that is able to alter transmission of action potentials in the nerve. In some instances, DC can be applied as a biphasic waveform, with the second phase operable to reverse the charge delivered by the first phase. In other instances, the second phase can reverse less than 100% of the total charge delivered by a first phase of the biphasic waveform to reduce electrochemical reactions that are damaging to the nerve and/or the electrode. In either circumstance, if the first phase of the biphasic waveform produces electrochemical reaction products, the second phase can reverse the electrochemical reaction products.

At Step 36, transmission of the action potentials in the target nerve can be altered (e.g., blocked or attenuated) based on the application of the DC. The transmission of the action potentials can be altered without damaging the structure of the nerve, the structure of the high-charge capacity electrode, and/or producing systemic side-effects.

V. Example

The following example is for the purpose of illustration only is not intended to limit the scope of the appended claims.

This Example demonstrates the feasibility of altering conduction in a rodent sciatic nerve using a carbon based high-charge capacity electrodes.

Methods

Figure 4:
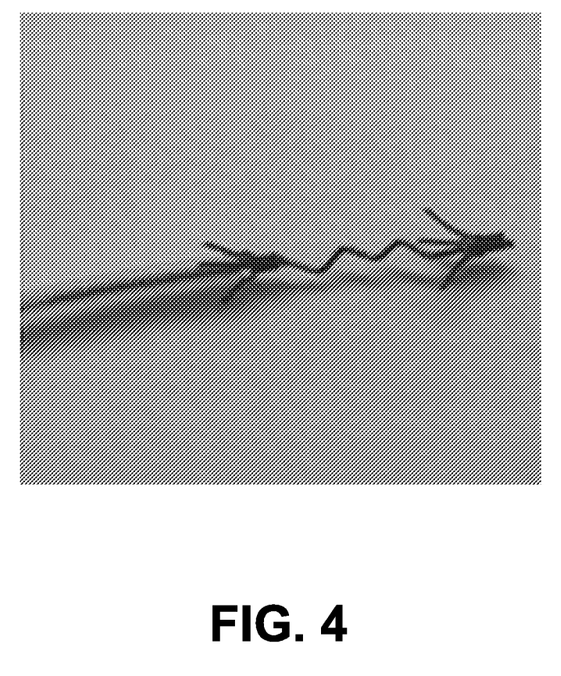
FIG. 4 is a photograph showing a prototype of a high-charge capacity electrode.

Carbon based high-charge capacity electrodes were constructed using YP-50 carbon active particles and polyvinylidene fluoride (PVDF) as a binder. Three grams of YP-50 were dispersed in 6 g of N-Methyl-2-pyrrolidone (NMP). To that dispersion, three grams of a 10 wt % solution of PDF in NMP were added. The resulting mixture was painted on to a platinum foil substrate (for the cuff electrode) and a platinum wire (for the wire electrode) and the NMP was removed by heating in air at 80° C. for 30 minutes. A photograph of the prototype of the carbon based high-charge capacity electrode is shown in FIG. 4.

Figure 5:
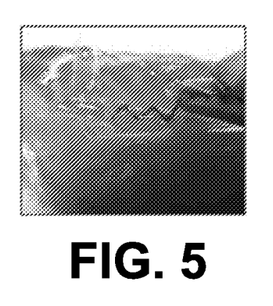
FIGS. 5-7 are photographs showing different configurations of the high-charge capacity electrode.
Figure 6:
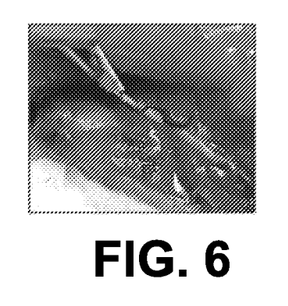
Figure 7:
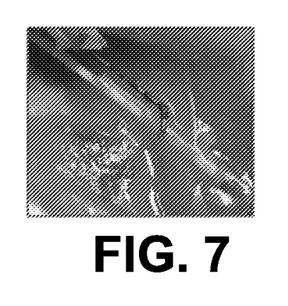

The carbon based high-charge capacity electrode is placed alongside the nerve. FIGS. 5-7 show examples of how the high-charge capacity electrode can be shaped and placed alongside the nerve to produce block. It was found that the most effective block occurred when the wire crosses approximately perpendicular to the long axis of the nerve, so these designs maximize the "perpendicular" feature.

A bipolar proximal stimulation electrode was placed proximally to a block electrode and used to elicit supramaximal muscle twitches. The blocking electrode (cuff electrode or the wire electrode) was placed around or near a rodent sciatic nerve in the middle. The blocking electrode applies the DC to block conduction in the nerve. The block was recorded distal to the blocking electrode.

Results

Figure 8:
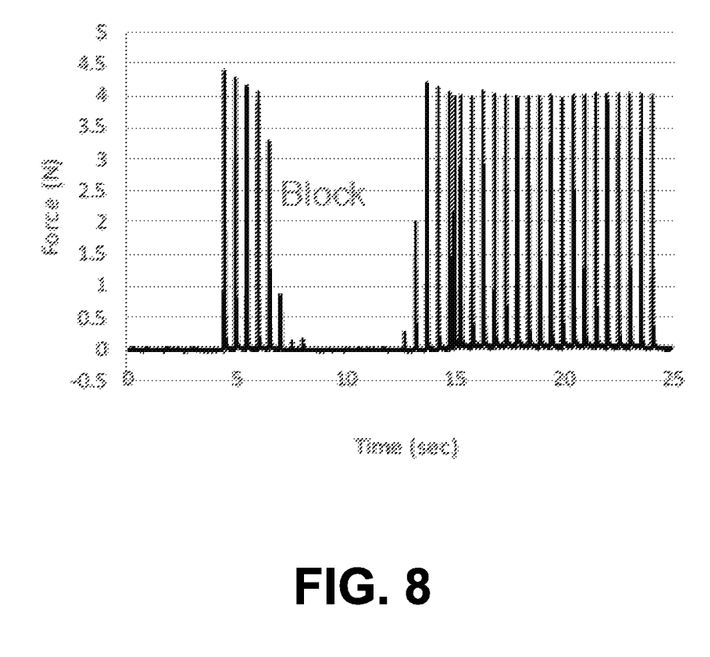
FIG. 8 is a graph showing complete sciatic nerve motor block with a wire high-charge capacity electrode.
Figure 9:
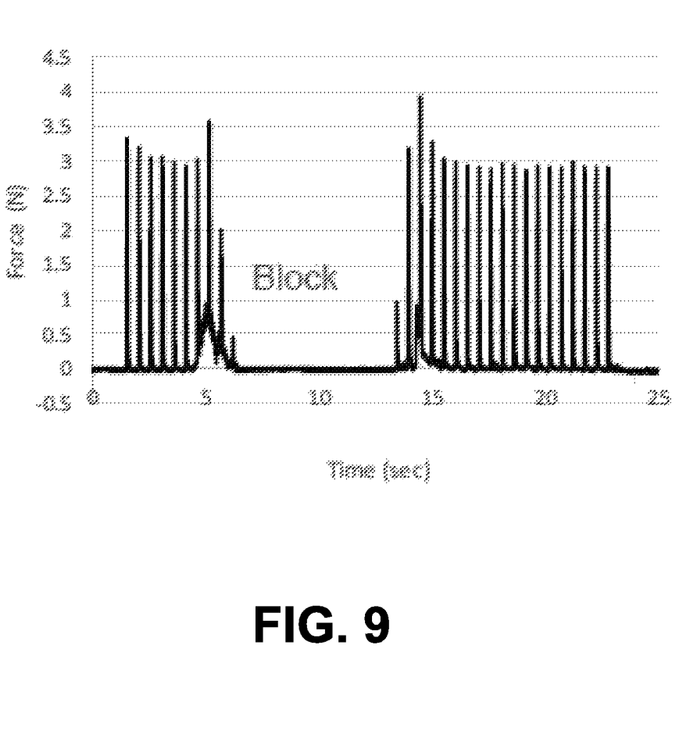
FIG. 9 is a graph showing complete sciatic nerve motor block with the high-charge capacity nerve cuff.

Prototype cuff and wire carbon based high-charge capacity electrodes were surgically placed in a rodent to block according to a rodent sciatic nerve model (perpendicular to the nerve). Complete nerve block was achieved, both with a wire carbon based high-charge capacity electrode (FIG. 8) and with the carbon based high-charge capacity electrode cuff (FIG. 9).

From the above description, those skilled in the art will perceive improvements, changes and modifications. Such improvements, changes and modifications are within the skill of one in the art and are intended to be covered by the appended claims.

The following is claimed:

1. A method, comprising:
   placing a high-charge capacity electrode, coupled to a current generator, in proximity to a nerve;
      wherein the high-charge capacity electrode comprises:
         an electrically conductive substrate; and
         a coating covering at least a portion of the substrate and adhering to the at least the portion of the substrate, wherein the coating is configured to be in contact with or exposed to the nerve;
         wherein the coating consists of active nano-particles held together by a biocompatible binder material that adheres to at least the portion of the substrate, and
         wherein the coating provides an electronic double layer capacitor (EDLC) configured to charge and discharge;
   applying a direct current (DC), generated by the current generator, to the nerve without generating damaging reaction products, wherein the DC has an amplitude sufficient to alter transmission of action potentials in the nerve and the DC is applied by discharging the EDLC without generating irreversible reaction products; and
   altering the transmission of the action potentials in the nerve based on the applied DC without causing damage to the nerve and/or the high-charge capacity electrode.

2. The method of claim 1, wherein the altering of the transmission of action potentials in the nerve comprises blocking the transmission of the action potentials in the nerve or attenuating the transmission of the action potentials in the nerve.

3. The method of claim 1, wherein the DC comprises a bi-phasic waveform.

4. The method of claim 3, wherein the bi-phasic waveform comprises a first phase that produces electrochemical reaction products and a second phase that reverses the electrochemical reaction products.

5. The method of claim 1, wherein the high-charge capacity electrode is placed alongside the nerve.

6. The method of claim 1, wherein the high-charge capacity electrode is placed perpendicular to a long axis of the nerve.

* * * * *